(12) United States Patent
Da Fonseca

(10) Patent No.: US 10,228,368 B2
(45) Date of Patent: Mar. 12, 2019

(54) ENHANCED SURFACE PLASMON RESONANCE METHOD

(71) Applicant: Biosurfit S.A., Aveiro (PT)

(72) Inventor: João Manuel Oliveira Garcia Da Fonseca, Azambuja (PT)

(73) Assignee: Biosurfit S.A., Aveiro (PT)

( * ) Notice: Subject to any disclaimer, the term of this patent is extended or adjusted under 35 U.S.C. 154(b) by 0 days.

(21) Appl. No.: 15/486,039

(22) Filed: Apr. 12, 2017

(65) Prior Publication Data

US 2017/0219571 A1     Aug. 3, 2017

Related U.S. Application Data

(62) Division of application No. 14/382,334, filed as application No. PCT/EP2013/054446 on Mar. 5, 2013, now Pat. No. 9,632,022.

(30) Foreign Application Priority Data

Mar. 5, 2012   (PT) .......................... 106192

(51) Int. Cl.
*G01N 33/543*     (2006.01)
*G01N 21/41*      (2006.01)
(Continued)

(52) U.S. Cl.
CPC ....... *G01N 33/54373* (2013.01); *G01N 21/41* (2013.01); *G01N 21/553* (2013.01);
(Continued)

(58) Field of Classification Search
CPC .................. G01N 21/41; G01N 21/553; G01N 2201/0612; G01N 2201/06146; G01N 2201/0621; G01N 2201/0635; G01N 2201/12723; G01N 33/4875; G01N 33/525; G01N 33/54346; G01N 33/54373; G01N 33/553; A61B 5/6898
USPC .............. 356/445–448, 128–137; 250/208.1, 250/208.2, 200, 206
See application file for complete search history.

(56) References Cited

U.S. PATENT DOCUMENTS 9,632,022 B2 *    4/2017   De Oliveira Garcia Da Fonseca ................. G01N 21/41
2003/0048452 A1   3/2003   Johansen
(Continued)

FOREIGN PATENT DOCUMENTS

DE     198 17 472 A1    10/1999
EP     1 684 063 A1      7/2006
(Continued)

OTHER PUBLICATIONS

PCT International Search Report and Written Opinion for PCT/EP2013/054446, dated Jun. 18, 2013, 9 pages.
(Continued)

*Primary Examiner* — Tri T Ton
(74) *Attorney, Agent, or Firm* — Patterson Thuente Pedersen, P.A.

(57) ABSTRACT

The disclosure relates to processing SPR signals, in particular signals obtained by illuminating a conductive surface with light at two wavelengths. Embodiments—involve processing a first and second signal indicative of an intensity of light, received from a conductive layer at which SPR has occurred, as a function of angle of incidence, reflection or diffraction at the layer (depending on whether the incident light beam is received by a detector recording it in reflection or transmission from the conductive layer). The first and second signals each have two dips corresponding to a respective wavelength of the light at a respective angle at which surface plasmon resonance occurs for the respective wavelength and a peak between the two dips. The processing includes deriving a first and second value of a quantity indicative of signal magnitudes in the region of the peak. The method then provides for comparing the first and second values to detect a change in refractive index at the layer after the first signal and before the second signal was captured.

13 Claims, 3 Drawing Sheets

(51) Int. Cl.
   *G01N 21/552*   (2014.01)
   *G01N 33/553*   (2006.01)

(52) U.S. Cl.
   CPC ..... *G01N 33/54346* (2013.01); *G01N 33/553* (2013.01); *G01N 2201/0612* (2013.01); *G01N 2201/0621* (2013.01); *G01N 2201/0635* (2013.01); *G01N 2201/06146* (2013.01); *G01N 2201/12723* (2013.01)

(56) References Cited

U.S. PATENT DOCUMENTS

| | | |
|---|---|---|
| 2007/0211985 A1 | 9/2007 | Duer |
| 2008/0037022 A1 | 2/2008 | Nishikawa et al. |
| 2008/0212102 A1 | 9/2008 | Nuzzo et al. |
| 2009/0231590 A1 | 9/2009 | Naya et al. |
| 2010/0271632 A1 | 10/2010 | Johansen |
| 2012/0120401 A1* | 5/2012 | Valsesia ............... G01N 21/274 356/445 |
| 2015/0109614 A1 | 4/2015 | Da Fonseca |

FOREIGN PATENT DOCUMENTS

| | | |
|---|---|---|
| EP | 1 967 844 A1 | 9/2008 |
| EP | 2 264 438 A1 | 12/2010 |
| WO | WO 2010/146367 A1 | 12/2010 |

OTHER PUBLICATIONS

Application and File history for U.S. Appl. No. 14/382,334, filed Sep. 2, 2014. Inventor: Da Fonseca.

\* cited by examiner

ENHANCED SURFACE PLASMON RESONANCE METHOD

PRIORITY CLAIM

This application is a division of application Ser. No. 14/382,334 filed Sep. 2, 2014, which is a National Phase entry of PCT Application No. PCT/EP2013/054446, filed Mar. 5, 2013, which claims priority from Portugal Application No. 106192, filed Mar. 5, 2012, the disclosures of which are hereby incorporated by referenced herein in their entirety.

FIELD OF THE INVENTION

The present invention relates to the detection of Surface Plasmon Resonance effects, in particular to detect changes in refractive index at a conductive surface, for example due to antibody/antigen binding events.

BACKGROUND OF THE INVENTION

The phenomenon of Surface Plasmon Resonance (SPR) can be used to detect minute changes in the refractive index at a surface of a conductive layer as some event occurs near the conductive surface, for example a metal coated surface. In particular it may be used to quantitatively determine a reaction between antigens (targets) and antibodies immobilised on the surface (probes). Surface Plasmon Resonance is due to the oscillation of free electrons which exists at a metal boundary induced by a time varying electric field absorbing photos of an incident light beam. These oscillations are affected by the refractive index of the material adjacent the metal surface and it is this that forms the basis of the sensor mechanism.

One of the most common SPR configurations involves the use of a polarized monochromatic light source (e.g. a diode laser) incident on the conductive layer, for example at the metal coated surface with a range of incident angles. In this configuration, one measures the light intensity of the reflected light beam as a function of angle over time while the event to be measured occurs, and detects a change of the angle at which a light intensity minimum occurs as a function of time.

For practical applications, SPR detection devices often include a cartridge having a liquid sample to be characterized. In many applications the cartridge is movable, in particular in some applications, the cartridge may rotate while SPR measurements are performed. SPR measurements may detect extremely small changes in a liquid sample (e.g. small concentration of a blood marker bound to corresponding probes), but may also be very sensitive to external effects (e.g. temperature, cartridge tilt and position, bulk effects). The latter can lead to a significant decrease in signal to noise ratios and so limit the application scope of SPR device.

Therefore, it would be desirable to have SPR devices providing better signal to noise ratios when compared to conventional devices. Furthermore, in the case of SPR devices including movable cartridges, it would be beneficial to have mechanisms for self-referencing and quality controls in order to ensure the quality of output data.

The specific description herein relates to a polarized double monochromatic light source incident on a detection zone. The double monochromatic light source has two wavelengths sufficiently similar so to induce the Surface Plasmon resonance effect at two similar incident angles, so that light can be captured for angles at which SPR occurs for both wavelengths, within a practical angular range. Two respective surface plasmons occur simultaneously over a predetermined critical incidence angle range and it is believed that their effect is combined to result in an increased light adsorption effect. Advantageously, the measurement of light reflection at the critical incidence angle range described herein shows a much greater sensitivity to events occurring in the liquid sample, compared with conventional known Surface Plasmon resonance devices. Furthermore, described herein are self-consistency tests associated to the double surface plasmon resonance measurements used for quality testing and feedback systems.

SUMMARY OF THE INVENTION

In a first aspect, there is provided a method for analysing a Surface Plasmon Resonance Signal as set out in independent claim 1.

Some embodiments include processing a first and second signal indicative of an intensity of light, received from a conductive layer at which SPR has occurred, as a function of angle of incidence, reflection or diffraction at the layer (depending on whether the incident light beam is received by a detector recording it in reflection or transmission from the conductive layer). The first and second signals each have two dips corresponding to a respective wavelength of the light at a respective angle at which surface plasmon resonance occurs for the respective wavelength and a peak between the two dips. The processing includes deriving a first and second value of a quantity indicative of signal magnitudes in the region of the peak. The method then provides for comparing the first and second values to detect a change in refractive index at the layer after the first signal and before the second signal was captured. Preferably, the step of detecting the change includes deriving a magnitude of the change.

Advantageously, this method is less sensitive to external effects, for example temperature, cartridge tilt and position, and bulk effects and, therefore, can provide improved signal to noise ratios.

It will be understood that reference to detecting a change (obtaining a magnitude of the change or merely that a change occurred) in refractive index includes doing so implicitly as the fundamental signal detectable by SPR, even if it is not explicitly calculated or detected. For example, the method may produce a result indicative of e.g. composition or concentration changes in a liquid sample of the conductive layer, such as targets binding to probes immobilised on the layer, temperature changes or any other changes affecting SPR. Further, the method may be equally applicable whether incident light is transmitted or reflected by the layer to reach a detector and irrespective of whether the beam path passes through a sample in contact with the liquid or not (e.g. by reflection from a surface of the layer not in contact with the sample). The method is equally applicable as an online method where signals are processed and changes detected as the signals are collected, or offline, where the signals are stored for later processing.

In some embodiments, the first signal was recorded before a sample is brought into contact with the layer and the second signal was recorded after the sample is brought into contact with the layer. It will be appreciated that in this way, the method allows a user to detect small changes of refractive index at the conductive layer due to a liquid sample. Preferably, probes are immobilised on the layer and the sample includes targets, such that the change in refractive index is due to targets binding to probes on the layer (and remaining there after a separate wash). This is particularly advantageous as the method can be used to detect small amounts of target present in a blood sample, blood plasma sample or other liquids.

In some embodiments, illumination may be provided at both wavelengths simultaneously and, additionally, the signals are captured at both wavelengths simultaneously. By capturing the signals at both wavelengths simultaneously, the signals required for the above processing can be captured in a simple and efficient way for example using an area detector, CCD array or a suitably placed photo multiplier tube. Further, due to the simultaneous illumination, it is believed that SPR effects may be enhanced.

The quantity indicative of signal magnitudes in the region of the peak may be the height of the peak and/or it may be the area under the signal between the peak and a threshold intensity level. The threshold intensity level may be determined by defining the intensity difference between two SPR dips and a pre-defined multiplicative or additive constant. By providing for a method which considers the change in peak height or area, the method provides for greater sensitivity and increased signal to noise ratios when compared to conventional methods which consider angular shifts in resonance angle or intensity measures locked onto certain angular positions. The measured quantity is directly based on the shape of the curve, rather than being indexed to a pre-defined angular position or relying on angle measurements.

Advantageously, the method may additionally provide for checking consistency between the first and second signals. This can be done by comparing at least two of the value of the quantity and the angle of each dip of the first signal to the same at least two of the second signal and checking if the respective changes between the first and the second signals are consistent. Such self-consistency checks may not be available or even possible with conventional Surface Plasmon Resonance techniques. By providing for a self-consistency check, quality assurance can be provided to ensure that the results obtained by the method are reliable. Furthermore, where the method finds that the results are not consistent, feedback control can used to make adjustments to correct the cause of inconsistency. For example, in some embodiments, the method allows the orientation of the conductive layer to be adjusted to ensure consistency.

In some embodiments, the conductive layer is provided on a cartridge. Advantageously this allows the conductive layer to be easily changed; thereby minimizing down time between uses of the Surface Plasmon Resonance device. The cartridge may comprise liquid handling structures to bring a liquid sample into contact with the conductive layer. The cartridge may be rotatable to drive liquid flow. The layer may comprise a grating profile.

The conductive layer may be configured as a suitable diffraction grating to achieve SPR momentum coupling, or a prism configuration may be used to achieve momentum coupling by total internal reflection.

In some embodiments, the method includes tuning one or both of the wavelengths (or a difference therebetween) to enhance signal to noise ratios, for example for a given grating configuration or prism coupling arrangement. The tuning may be by means of cooling or heating (or both) element placed in between two laser diodes emitting at respective wavelengths and changing losing behaviour to control wavelength by temperature control. The diodes may intrinsically emit at the same wavelengths (the difference being established by a temperature difference) or at different wave-lengths (still tuning the difference using temperature).

In a second aspect, there is provided a method for detecting a change in refractive index.

Some embodiments comprise simultaneously illuminating a conductive surface with light at two wavelengths and measuring an intensity of light returned from the conductive surface at angles lying between an angle at which a first intensity minimum due to Surface Plasmon Resonance at one of the wavelengths occurs and an angle at which a second intensity minimum due to Surface Plasmon Resonance at the other one of the wavelengths occurs and detecting a change in the refractive index by detecting a change in the measured intensity.

In some embodiments, the step of detecting the change includes quantifying a concentration of target molecules in a sample applied to the conductive surface based on change in the measured intensity. The simultaneous illumination may be provided by separate monochromatic sources, such as two lasers, laser diodes or LEDs, combined using a beam splitter (possibly also using suitable filtering). A single source with suitable spectral lines may be used instead.

In third and fourth aspects there are provided systems configured to implement methods as described above.

BRIEF DESCRIPTION OF THE DRAWINGS

Embodiments are now described by way of example only to illustrate aspects and principles of the present disclosure, with reference to the accompanying drawings in which.

DETAILED DESCRIPTION OF THE DRAWINGS

Figure 1:
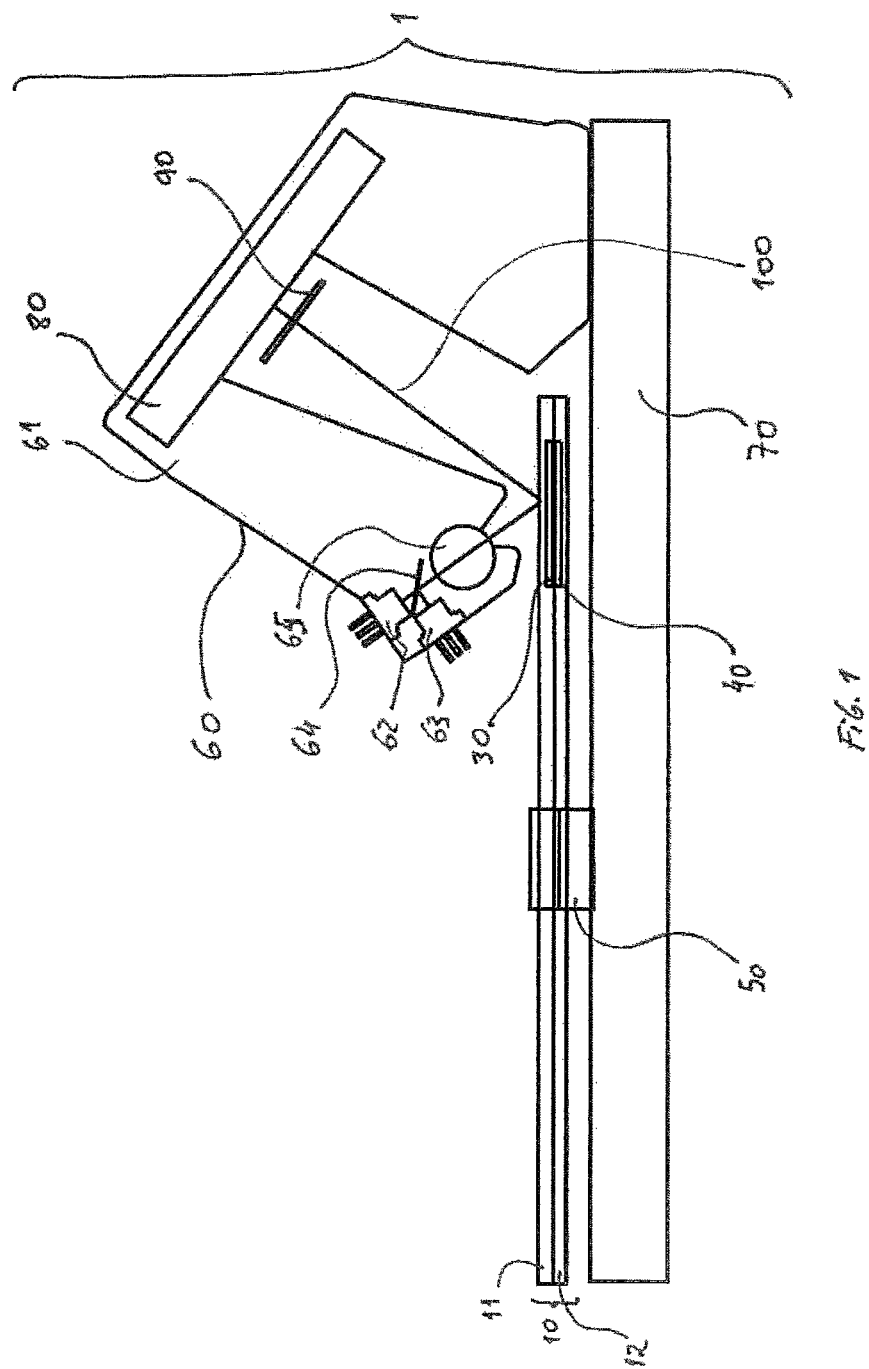
FIG. 1 illustrates a device (1) comprising a rotatable cartridge (10) attached to a motor (50) and an optical module (60); wherein the motor (50) and the optical module (60) are both attached to a base (70). The optical module (60) comprises two laser diodes (62) and (63) aligned perpendicular to each other and a beam splitter (64) which is capable of combining the laser diode beams.

FIG. 1 illustrates a device (1) comprising rotatable cartridge (10) which is releasably attachable to a motor (50). The device (1) further comprises an optical module (60). Both the motor (50) and optical module (60) are preferably attached to a base (70). The optical module (60) comprises two laser diodes (62) and (63) which are preferably aligned perpendicular to each other. Preferably, the optical module (60) comprises a beam splitter (64) suitable for combining the laser diode beams.

The light beam (100) coming from the beam splitter (64) is focused on a detection zone (30) on the cartridge (10). A grating surface (40) consisting of a grating dielectric with a predetermined grating profile covered by a thin metal layer may be provided on the cartridge (10) to provide a conductive layer acting as a detection surface for generating a Surface Plasmon Resonance effect. The light beam (100) is then incident on an optical element (90), for example a lens, and then on an optical detector (80).

Preferably, the detection zone (30) may contain a sample liquid with specific biological elements to be quantitatively measured by the device (1). Preferably, the cartridge (10) comprises two plastic parts (11) and (12) which may be bonded together. The cartridge (10) is arranged such that while it is being rotated by action of the motor (50), the light beam (100) can be detected by the optical detector (80).

Figure 2:
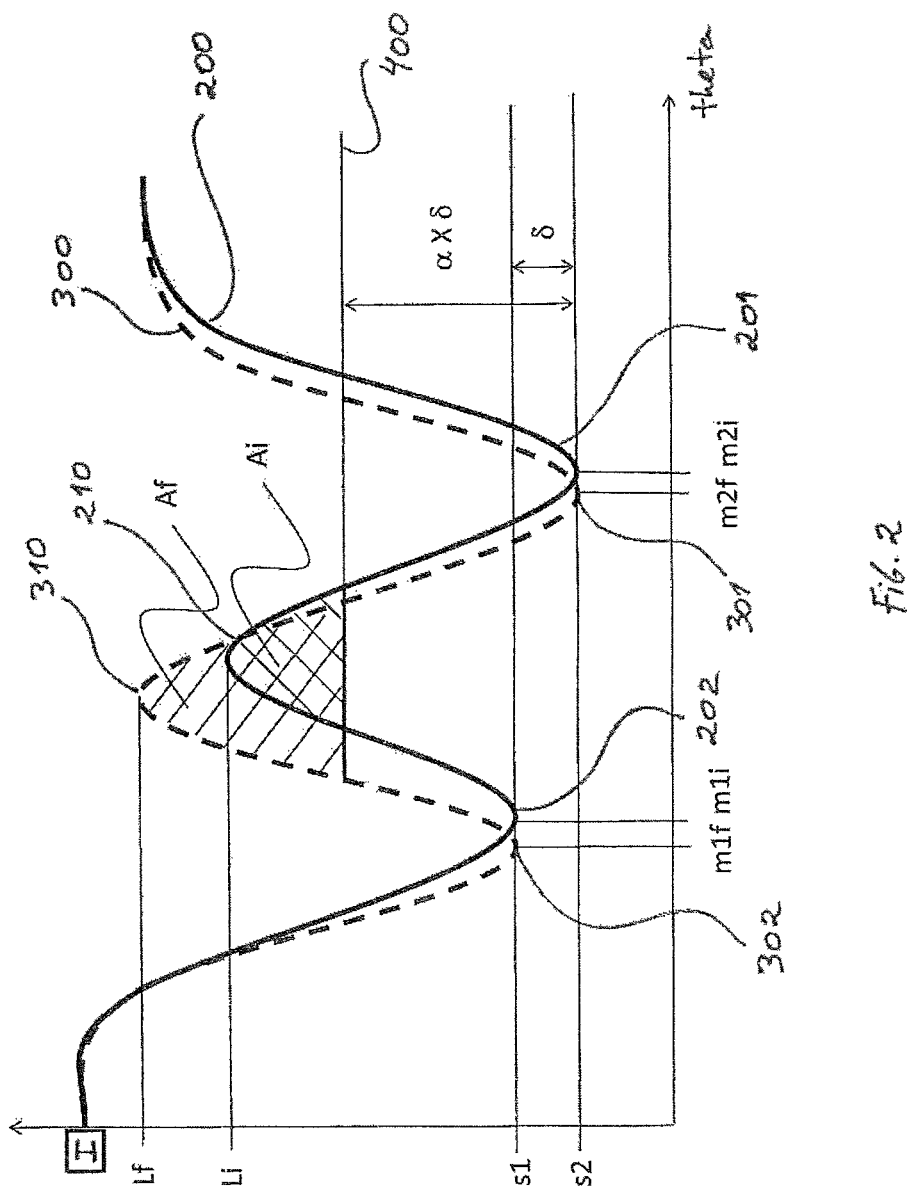
FIG. 2 illustrates two output light intensity signals detected by the optical detector (80) of device (1) as illustrated in FIG. 1, as a function of the incident angle at the optical detector (80)

FIG. 2 illustrates two output light intensity signals detected by the optical detector (80) of the device (1) described above in respect of FIG. 1, as a function of the incident angle at the optical detector (80). As illustrated in FIG. 2, the first light intensity output signal (200) comprises two dips (201) and (202) which correspond to the Surface Plasmon Resonance effect of each light source (62) and (63). Preferably, the device (1) is configurable to allow, a set of parameters to be adjusted; including but not limited to: the grating profile (i.e. grating period, grating height and profile shape), the range of incident angles and the wavelength difference between the two monochromatic sources (62) and (63). As depicted in FIG. 2, in between the two Surface Plasmon Resonance dips (201) and (202) there is a light intensity peak (210). Due to the difference of wavelengths of the two monochromatic sources, the two dips (201) and (202) have different light intensity values.

The analytical device (1) may be used to probe or quantify events or elements in a liquid sample placed or flowing into at least one detection zone (30), and measurements maybe performed as a function of time. Preferably the device (1) determines a sensorgram, thereby providing the temporal variation of at least one parameter which affects Surface Plasmon Resonance.

The sensorgram may depict the angle of incidence corresponding to the minimum of the Surface Plasmon Resonance dip (201) of a light intensity output signal as a function of, e.g. incident, angle over time.

Continuing the detailed description of FIG. 2, the curve (300) represents the light intensity output signal detected in the optical detector (80) after a period of time when the signals of the curve (200) was detected. A certain event occurring in the liquid sample, for example, the binding of a blood marker with a specific antibody coated on the thin metal layer of the grating surface (40) (and preferably a subsequent wash to remove excess sample). The change in refractive index of the grating surface (40) associated with the event leads to a change of angular position of the minima of dips (301) and (302) compared to curve (200). Conventional methods relate to quantifying this shift, represented by the angular distance between m1i and m1f for one wavelength and the distance between m2i and m2f for the other wavelength.

The method described herein explores a change of the peak of light intensity of the output light signal (210) to (310), located in between the two Surface Plasmon Resonance dips. This will be noted from FIG. 2 which illustrates a much more marked change of the peak (210) to peak (310), when compared to the changes of each Surface Plasmon Resonance dips.

The observed fact that both Surface Plasmon resonance dips originated each by one of the monochromatic light sources (62, 63) have significantly different minimum intensity may further be explored in order to enhance the change signal calculated by the device (1). By measuring the difference δ in intensity between each dip (201) and (202), defined by s1 and s2 in FIG. 2, the device (1) determines a threshold level (400) and calculates the total area of the peak above that threshold. The threshold is in some embodiments calculated as a factor at times the difference S.

The area Ai changes into area Af while the event to be detected by the device (1) occurs. Detection of the change in area may be done with a sensitivity increased by many orders of magnitude when compared to the angular shift between m2i and m2f, which is the only information used by conventional methods.

The analytical method described herein, explores this novel effect, associated with the asymmetric change of each Surface Plasmon Resonance dip for the two-wavelength intensity signal.

An additional advantages of the method described herein, is due to the fact that the claimed method measures light which is easier than measuring dark, thereby enabling a further increase in the signal to noise ratio.

Further described herein is a method of self-consistency checking provided by the device (1) to overcome quality control issues occurring in conventional Surface Plasmon Resonance devices. One important aspect associated with Surface Plasmon Resonance analytical devices relates to consistency and quality controls.

Figure 3:
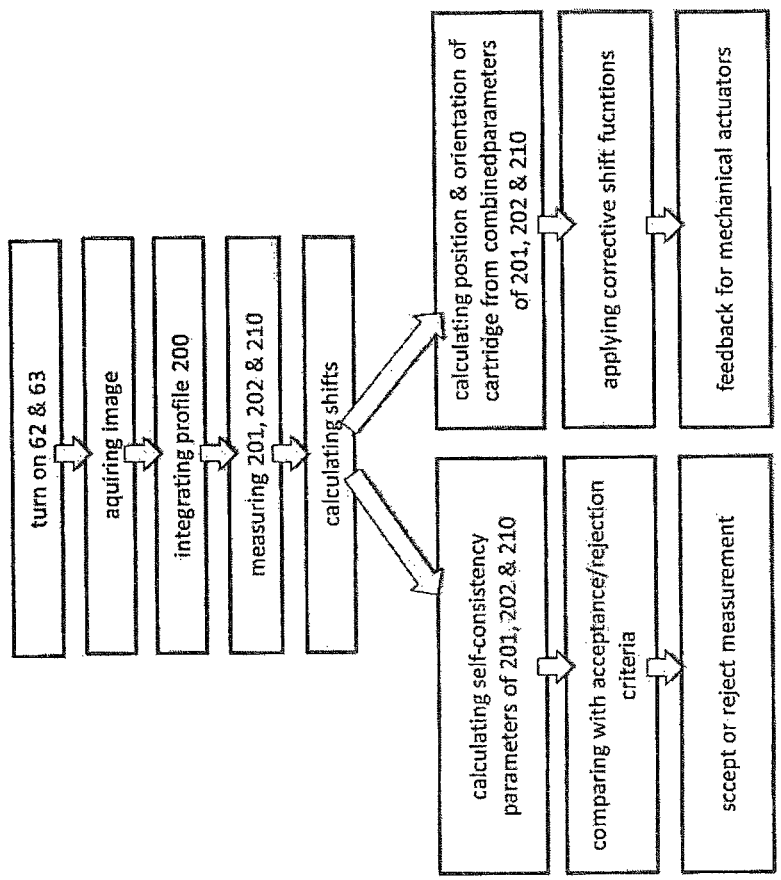
FIG. 3 illustrates an operating protocol of a device (1).

By exploring known correlations between features detected in the output signal and illustrated in FIG. 3, the device (1) may be used with built-in self-consistency checks. These checks may include acceptance and rejection criteria for accepting or rejecting measurements from specific detection zones having non-consistent output signals. In one example of correlations used for self-consistency checks, if the shift or change of the dip m2 is significantly smaller or larger than the shift or change of m1 then measurements are not deemed to be self-consistent. In another examples if both shifts of m1 and m2 are consistent but the shift of the peak intensity L is significantly smaller or larger when compared to an expected shift obtained from correlation with the shifts of m1 and m2, then measurements are also not deemed to be self-consistent.

FIG. 3 illustrates an operating protocol of the device (1).

Non consistency of each output parameter may arise from different effects; for example, variations may occur depending on the orientation or position of the cartridge (10) with respect to the optical module (60), particularly if it is outside an acceptable range. The device (1) described herein may be operated in such a way that measurements of correlated parameters of output data can be used to determine the relative position of the cartridge (10) and/or its orientation with respect to the optical module (60), thereby allowing corrective algorithms for measured shifts to be applied. Furthermore, having determined the position and orientation of the cartridge (10), the device (1) may be arranged in such a manner as to induce feedback correction actions by mechanical actuators.

One specific, embodiment of a device and method is described.

The cartridge (10) consists of two disk-shape polycarbonate parts of 0.6 mm thickness each bonded together, having an outer diameter of 120 mm and an inner hole of 15 mm diameter centred at the rotational axis of the motor (50). The cartridge contains 30 detection zones (30) each of 0.02 mm depth engraved into the upper cartridge part (11) having an average radius of 50 mm from the rotational axis and being capable of holding 0.2 uL of blood. It will be appreciated that the cartridge need not be provided in a disk shape and the dimensions and materials of the cartridge described herein are illustrative only.

While the cartridge is rotated, the liquid sample, consisting of diluted blood plasma, flows from upstream chambers into downstream chambers passing each detection zone (30). Preferably, the cartridge is rotated at around 25 Hz. The lower part (12) of the cartridge (10) may contain a grating at the detection zones (30) which is in some embodiments a sine-trapezoidal shape. More particularly, the grating may have a grating period of 950 nm and a grating height of 50 nm in some embodiments. The grating is defined in the polycarbonate part (12) and maybe coated by 100 nm of gold, wherein antibodies are attached. It will be appreciated that other suitable coating may be provided which allows for antibodies to attach thereto.

The optical module (60) contains two diode lasers (62) and (63) in some embodiments. In an illustrative example, the diode lasers emit at 785 nm and 808 nm, and are aligned perpendicularly. A beam splitter consisting of a glass plate of 0.1 mm of thickness and 15 nm of reflective metal layer, with the thickness adjusted in order to have ~50% of light transmission at ~800 nm of wavelength is provided. An acrylic cylinder (65) preferably focuses the light beam (100) into the grating surface (40) of the detection zone (30). The first order reflective diffraction passes into a polarizer (90) and is incident into the optical detector, preferably a CMOS camera (80). The camera can detect the output light signal over ~3° of angular range, centred at ~55° with respect to a plane of the grating surface (40). It will be appreciated that other suitable specifications and arrangements of diode laser, beam splitter and optical detector may be provided.

The motor (50) may be a standard BLDC motor, which can be controlled with rotational speeds between 5 Hz and 150 Hz. Both the motor (50) and the optical module (60) can be attached to a base (70) and the whole system is preferably temperature controlled by external components.

When the motor is rotated, at 25 Hz in one example, a first buffer liquid, which consists of PBS 1× (or any other suitable buffer), in this example, can flow through the detection zones (30) at a roughly constant flow rate. The acquired signal is represented by the curve (200) in FIG. 2. Then the sample diluted blood plasma flows through the detection zone and finally a buffer liquid preferably consisting of PBS 1× flows again through the detection zone (30), washing and making a final baseline signal represented in FIG. 2 by the curve (300).

The observed change is substantially proportional to the concentration of an analyte having bound to antibodies immobilised on the grating surface of a detection zone (30).

The intensities and angular positions of the dips and peaks may be further analysed for self-consistency as described above and the measurement(s) may be accepted or rejected depending on the observed values and criteria.

In some embodiments, the two Surface Plasmon Resonance dips are expected to occur centred at respective angles, for example 54.5° and 55.5°. Several experimental effects may lead to different values for the two Surface Plasmon Resonance dips, such as: bending or orientation of the cartridge, temperature of the system, liquid sample concentration, biological coating, etc. In one example, the system is defined with an acceptance criteria as an angular tolerance, e.g. of +/−0.1°, meaning that the measurement is accepted only if the measured dip angles have a difference consistent with the respective angular tolerance, e.g. of 1°+/−0.1°. In a further example, the acceptance criteria includes also or instead an absolute angle criteria, for example requiring an angular spacing of 1°+/−0.1° and a centre of each dip at specific angles, e.g. 54.5° and 55.5°, respectively. Measurements would be rejected in this latter case, if the two dips had an angular spacing of 1°+/−0.1° but were centred around 54.5° and 55.5°, respectively. This could in practice occur if, for example, the cartridge had a tilted orientation with respect to its expected orientation.

In particular embodiments, a cartridge orientation tilted at a certain angular value [e.g. 5°] would lead to an equivalent shift of both SPR dips [e.g. the same 5°] due to the corresponding tilt of the conductive layer/detection surface. This tilted orientation could then be easily determined by observing the initial angular positions of the two SPR dips. This tilted orientation may be then considered, in some implementations, irrelevant for the quality of the measurements, provided that there is consistency in the relative angular position of the dips. In other embodiments, the tilted orientation of the cartridge could be considered important for the acceptance of measurements, even if both SPR dips are observed to be mutually spaced within the acceptable angular range. One could then reject measurements by defining and implementing specific acceptance criteria accordingly.

Furthermore, in specific embodiments, a feedback loop applies commands to action mechanical actuators in order to correct the orientation of the cartridge (and hence the conductive layer/detection surface). For example, a feedback mechanism is in some embodiments implemented as follows: (i) confirm the two SPR dips are spaced within the acceptable range; (ii) find an angular deviation of dip centre position from the expected position, e.g. 2°; (iii) tilt the optical module (60) by the determined deviation to bring the two SPR dips to their expected angular position; (iv) perform further measurements in accordance with the embodiments described above.

Several possible correlations for quality control may be derived depending on the application and, each particular implementation of the Surface Plasmon Resonance detection system. Correlations rely on the expected common shapes of optical signals resulting from similar but slightly different two Surface Plasmon Resonance dips. Self-consistency parameters need to be observed in order to accept specific measurements in such embodiments.

In one specific implementation, the SPR dips need to be within a predefined angular position [e.g. 54.5°+/−0.1° for the first SPR dip and 55.5°+/−0.1° for the second SPR dip] for the initial SPR measurements prior to passing a sample and the mutual spacing between the two SPR dips need to be within another predefined angular range [e.g. 1.0°+/−0.1°]. In this case measurements are rejected if they do not comply with the acceptance criteria.

In another specific implementation example, additionally or alternatively, the intensity level of the initial peak Ai between the two SPR deeps need to be a pre-defined fraction of the maximum measured light intensity, for example 70%+/−1% of the maximum measured light intensity.

Measurements are rejected if they do not comply with all the applicable acceptance criteria, in some embodiments.

In other specific implementation examples, other or additional criteria may be preferable, for example where further additional acceptance criteria are necessary for accepting measurements. Additional relevant acceptance criteria may include, but are not limited to, the relative difference of light intensity of the two SPR dips; the relative angular spacing between the initial peak Ai and the two SPR dips m1i and m2i; the relative difference of shift of each of the two SPR dips, etc.

In some embodiments, the diode lasers (62) and (63) may be identical or emit intrinsically at the same wave length. Further an additional peltier thermoelectrical module is placed in between the two laser diodes in these embodiments, and operated in such a way as to induce a temperature difference between the diodes (62) and (63). This temperature difference leads to a significant difference lasing wavelength, in view of the known dependency of the lasing wavelength with temperature. By varying the temperature differences between the elements (62) and (63), the induced temperature difference may be turned in order to maximize the double surface Plasmon resonance effect described above. The same arrangement may also be used to tune the wavelength difference between two laser diodes intrinsically emitting at the same frequency.

In some embodiments, the detection surface has a grating surface of a sinusoidal shape, trapezoidal shape or triangular shape, instead of a sine-trapezoidal shape. Each specific shape of the grating surface will result in a different and characteristic shape of each SPR dip, in particular expected SPR dip width and symmetry. Accordingly, where quality or feedback control as described above is employed, the parameters of acceptance criteria are adjusted for each particular grating implementation.

Alternatively, in some embodiments, detection systems have a detection surface with a flat conductive surface and use a prism configuration to achieve the momentum coupling required for SPR to occur. In this later case, the SPR dips have a known pre-defined shape. Again, if quality or feedback control is used, the acceptance criteria need to be adjusted to this particular implementation.

It will be appreciated that the invention is not limited to any specific type of cartridge dimensions, configurations or materials, or to a specific number detection zones.

For the avoidance of doubt, the term "microfluidic" is referred to herein to mean devices having a fluidic element such as a reservoir or a channel with at least one dimension below 1 mm.

It will also be appreciated that the present invention is not intended to be limited by the particular described embodiments and examples.

The invention claimed is:

1. A method for analysing a Surface Plasmon Resonance Signal, the method comprising:
    processing a first signal indicative of an intensity of light, received from a conductive layer at which SPR has occurred, as a function of angle of incidence, reflection or diffraction at the layer, the first signal having two dips corresponding to a respective wavelength of the light at a respective angle at which surface plasmon resonance occurs for the respective wavelength and a peak between the two dips, wherein the processing includes deriving a first value of a quantity indicative of signal magnitude in the region of the peak;
    processing a second signal indicative of an intensity of light, received from a conductive layer at which SPR has occurred, as a function of angle of incidence, reflection or diffraction at the layer, the second signal having two dips corresponding to a respective wavelength of the light at a respective angle at which surface plasmon resonance occurs for the respective wavelength and a peak between the two dips, wherein the processing includes deriving a second value of a quantity indicative of signal magnitude in the region of the peak; and
    comparing the first and second values to detect a change in refractive index at the conductive layer after the first signal and before the second signal was captured.

2. The method of claim 1, wherein detecting the change includes deriving a magnitude of the change.

3. The method of claim 2, wherein the first signal was recorded before a sample is brought into contact with the layer and the second signal was recorded after the sample is brought into contact with the layer.

4. The method of claim 3, wherein probes are immobilised on the layer and wherein the sample comprises targets, such that the change in refractive index is due to targets binding to probes on the layer.

5. The method of claim 1, further comprising providing illumination at both wavelengths simultaneously and capturing the signals at both wavelengths simultaneously.

6. The method of claim 1, wherein the quantity indicative of signal magnitudes in the region of the peak comprises the area under the signal between the peak and a threshold intensity level.

7. The method of claim 6, wherein the threshold intensity level is proportioned to a difference between respective signal magnitudes at the dips.

8. The method of claim 1, wherein the quantity indicative of signal magnitudes in the region of the peak comprises the height of the peak.

9. The method of claim 1, further comprising checking consistency between the first and second signals by comparing at least two of the value of the quantity and the angle of each dip of the first signal to the same at least two of the second signal.

10. The method of claim 1, further comprising comparing respective values of one or more parameters measured from the first signal, the second signal, or both to expected respective values of the one or more parameters and, preferably, rejecting the signals if the respective values do not match, and, additionally or alternatively, adjusting an orientation of the conductive layer to make the respective values match.

11. The method of claim 1, wherein the conductive layer is provided on a cartridge comprising liquid handling structures for bringing a sample into contact with the conductive layer.

12. The method of claim 11, wherein the cartridge is rotatable to drive liquid flow in the cartridge.

13. The method of claim 1, wherein the conductive layer comprises a grating profile.

* * * * *